United States Patent
Muraoka et al.

(10) Patent No.: US 11,874,260 B2
(45) Date of Patent: *Jan. 16, 2024

(54) PROVIDING SYSTEM, SCENT IMPARTING APPARATUS, SCENT DETECTING APPARATUS, AND INFORMATION MANAGEMENT APPARATUS

(71) Applicant: Panasonic Intellectual Property Management Co., Ltd., Osaka (JP)

(72) Inventors: Junko Muraoka, Kyoto (JP); Shikiho Kawai, Hyogo (JP); Kosuke Nakajima, Osaka (JP); Jin Muraoka, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 230 days.

This patent is subject to a terminal disclaimer.

(21) Appl. No.: 17/371,152

(22) Filed: Jul. 9, 2021

(65) Prior Publication Data
US 2021/0333253 A1 Oct. 28, 2021

Related U.S. Application Data

(63) Continuation of application No. PCT/JP2020/006224, filed on Feb. 18, 2020.

(30) Foreign Application Priority Data

Mar. 13, 2019 (JP) .................................. 2019-045648

(51) Int. Cl.
*G01N 33/00* (2006.01)

(52) U.S. Cl.
CPC ..... *G01N 33/0001* (2013.01); *G01N 33/0098* (2013.01)

(58) Field of Classification Search
CPC ........... G01N 33/0001; G01N 33/0098; G01N 2033/4977; G01N 33/48; G01N 33/025; G06Q 50/02
(Continued)

(56) References Cited

U.S. PATENT DOCUMENTS

| 2014/0041533 A1* | 2/2014 | Minvielle | A23P 10/00 99/486 |
| 2014/0127672 A1* | 5/2014 | Davis | C12Q 1/689 435/6.12 |

(Continued)

FOREIGN PATENT DOCUMENTS

| DE | 60023636 T2 * | 7/2006 | G01N 3/40 |
| JP | 3585172 B2 * | 11/2004 | |

(Continued)

OTHER PUBLICATIONS

Communication pursuant to Article 94(3) EPC dated Jun. 3, 2022 for the related European Patent Application No. 20 771 063.3.
(Continued)

*Primary Examiner* — Marrit Eyassu
(74) *Attorney, Agent, or Firm* — Wenderoth, Lind & Ponack, L.L.P.

(57) ABSTRACT

A scent imparting apparatus transmits to an information management apparatus, product information that includes added-substance information indicating a first substance that is a scented substance added to a plant and production information regarding the plant. The information management apparatus stores the received product information in a production information storage unit. A scent detecting apparatus detects a second substance that is at least one of the scented substance or a metabolite of the scented substance released from a target plant, and transmits detected-substance information indicating the second substance to the information management apparatus. The information man-
(Continued)

agement apparatus transmits to the scent detecting apparatus, in a case where the second substance indicated by the received detected-substance information is the same as the first substance indicated by the added-substance information included in the product information stored in the production information storage unit or is the same as a metabolite of the first substance, the production information included in the product information stored in the production information storage unit. The scent detecting apparatus presents the received production information.

8 Claims, 9 Drawing Sheets

(58) Field of Classification Search
USPC .......................................................... 73/23.34
See application file for complete search history.

(56) References Cited

U.S. PATENT DOCUMENTS

2019/0137476 A1* 5/2019 Davis .................... B01D 53/025
2021/0333252 A1* 10/2021 Muraoka ................ G01N 33/48

FOREIGN PATENT DOCUMENTS

| JP | 2006-504491 | | 2/2006 | |
|---|---|---|---|---|
| JP | 2006036980 | A * | 2/2006 | |
| JP | 2008-165504 | | 7/2008 | |
| JP | 2011-090435 | | 5/2011 | |
| WO | 2004/041328 | | 5/2004 | |
| WO | 2007/002768 | | 1/2007 | |
| WO | WO-2020016193 | A1 * | 1/2020 | ............. A01N 25/00 |

OTHER PUBLICATIONS

International Search Report of PCT application No. PCT/JP2020/006224 dated May 19, 2020.

* cited by examiner

FIG. 5

| PRODUCT LOT | HARVESTING DATE | PRODUCT NAME | GROWER INFORMATION | TYPE OF SCENT | TYPE OF METABOLITE | SCENT IMPARTING DATE AND TIME | SCENT DETECTION RESULT | SCENT DETECTING PERSON | SHIPPING DATE AND TIME | DESTINATION OF SHIPMENT | TRANSPORT OPERATOR |
|---|---|---|---|---|---|---|---|---|---|---|---|
| S00001 | 4/1 | STRAWBERRY | AA | X | X1 | 4/1 10:00 | DETECTED | CC | 4/1 15:00 | EE | GG |
| S00002 | 4/2 | STRAWBERRY | BB | Y | Y1 Y2 | 4/2 11:00 | DETECTED | DD | 4/2 16:00 | FF | HH |
| ⋮ | ⋮ | ⋮ | ⋮ | ⋮ | ⋮ | ⋮ | ⋮ | ⋮ | ⋮ | ⋮ | ⋮ |

FIG. 7

Product information input screen — 151

| Grower information | | Type of scent | X |
| Harvesting date | / / | Type of metabolite | |
| Product name | | Scent imparting date and time | X/X X:XX |
| | | Scent detecting person | |
| Shipping date and time | / / | | |
| Destination of shipment | | Product lot | |
| Transport operator | | | |

Transmit (152)  Exit (153)

FIG. 9

Production information  〔341  〔343

| | | |
|---|---|---|
| Product lot | S00001 | Exit |
| Grower information | AA | |
| Harvesting date | 4/1 | |
| Product name | Strawberry | |
| Shipping date and time | 4/1 15:00 | |
| Destination of shipment | EE | |
| Transport operator | GG | |

FIG. 10

Traceability information input screen  〔344

| | |
|---|---|
| Product lot | |
| Product name | |
| Scent detection date and time | X/X X:XX |
| Scent detecting person | |
| Type of scent/metabolite | X |

Transmit  345

Exit  346

Traceability result screen

Production information

| | |
|---|---|
| Product lot | S00001 |
| Grower information | AA |
| Harvesting date | 4/1 |
| Product name | Strawberry |
| Shipping date and time | 4/1 15:00 |
| Destination of shipment | EE |
| Transport operator | GG |

Exit

Detection result information

| | |
|---|---|
| First scent detection | Detected |
| Second scent detection | Detected |
| Third scent detection | Detected |

PROVIDING SYSTEM, SCENT IMPARTING APPARATUS, SCENT DETECTING APPARATUS, AND INFORMATION MANAGEMENT APPARATUS

BACKGROUND

1. Technical Field

The present disclosure relates to an information providing method for providing information regarding a plant, an information providing system that provides information regarding a plant, a scent imparting apparatus that adds a scented substance to a plant, a scent detecting apparatus that detects a substance released from a plant, and an information management apparatus that manages information regarding a plant.

2. Description of the Related Art

Recently, there has been a demand for providing fresh food products with production information including the grower and the harvesting date in order to provide safe fresh food products to consumers.

For example, Japanese Unexamined Patent Application Publication No. 2008-165504 discloses a production information communicating method in which production information of a fresh food product is converted to a two-dimensional barcode, the fresh food product provided with the two-dimensional barcode is put on sale via a distribution channel, a person who wants to purchase the fresh food product put on sale photographs the two-dimensional barcode of the fresh food product with a digital camera, and the production information of the fresh food product obtained by decoding the photographed two-dimensional barcode is displayed.

For example, Japanese Unexamined Patent Application Publication (Translation of PCT Application) No. 2006-504491 describes a pharmaceutical product having a scent for establishing the identity and/or supply source of the pharmaceutical product.

SUMMARY

However, with the existing techniques described above, it is difficult to have a plant itself present production information regarding the plant, and there has been a demand for further improvement.

One non-limiting and exemplary embodiment provides a technique for making it possible to have a plant itself present production information regarding the plant.

In one general aspect, the techniques disclosed here feature an information providing method for an information providing system including a scent imparting apparatus, a scent detecting apparatus, and an information management apparatus, the information providing method including: adding, by the scent imparting apparatus, a scented substance to a plant; transmitting, by the scent imparting apparatus to the information management apparatus, product information that includes added-substance information indicating a first substance that is the scented substance and production information regarding the plant; receiving, by the information management apparatus, the product information; storing, by the information management apparatus, the product information in a production information storage unit; detecting, by the scent detecting apparatus, a second substance that is at least one of the scented substance or a metabolite of the scented substance released from a target plant; transmitting, by the scent detecting apparatus to the information management apparatus, detected-substance information indicating the second substance; receiving, by the information management apparatus, the detected-substance information; transmitting, by the information management apparatus to the scent detecting apparatus, in a case where the second substance indicated by the received detected-substance information is the same as the first substance indicated by the added-substance information included in the product information stored in the production information storage unit or is the same as a metabolite of the first substance, the production information included in the product information stored in the production information storage unit; receiving, by the scent detecting apparatus, the production information from the information management apparatus; and presenting, by the scent detecting apparatus, the received production information.

According to the present disclosure, it is possible to have a plant itself present production information regarding the plant.

It should be noted that this general or specific aspect may be implemented as an apparatus, a system, an integrated circuit, a computer program, or a computer-readable recording medium or may be implemented as a combination of any of an apparatus, a system, a method, an integrated circuit, a computer program, and a computer-readable recording medium. Examples of a computer-readable recording medium include a non-volatile recording medium, such as a CD-ROM (compact disc read-only memory).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 5 is a diagram illustrating an example of product information stored in a product information storage unit in the present embodiment;

FIG. 7 is a diagram illustrating an example of a product information input screen in the present embodiment;

FIG. 9 is a diagram illustrating an example of presentation information including production information in the present embodiment;

FIG. 10 is a diagram illustrating an example of a traceability information input screen in the present embodiment;

DETAILED DESCRIPTION

Figure 1:
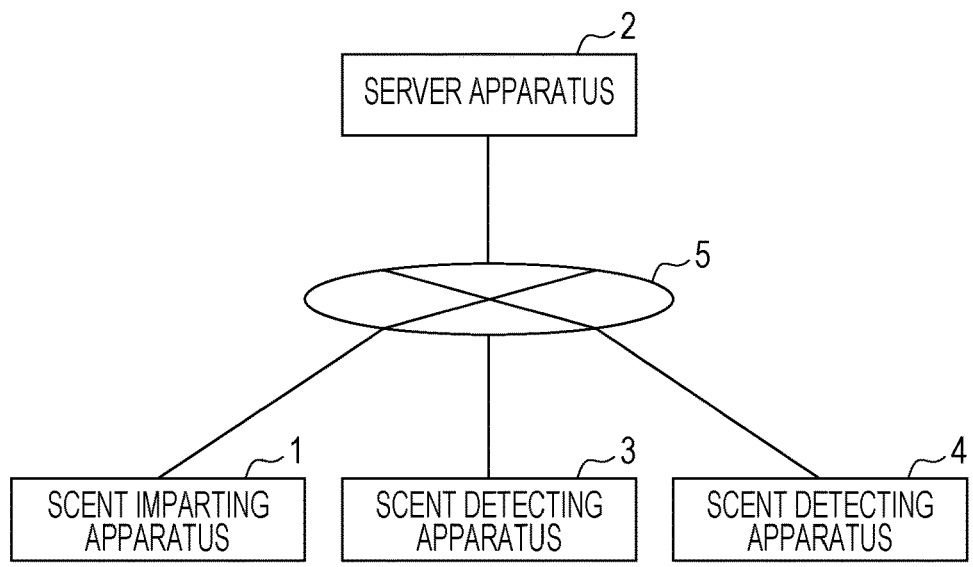
FIG. 1 is a diagram illustrating an overall configuration of an information providing system in the present embodiment.

Underlying Knowledge Forming Basis of the Present Disclosure

In Japanese Unexamined Patent Application Publication No. 2008-165504, production information of a fresh food product is converted to a two-dimensional barcode, the two-dimensional barcode is printed on an adhesive label, and the label is affixed to the fresh food product. In this case, the two-dimensional barcode is not printed on the fresh food product itself, and therefore, the label can be forged and the forged label can be affixed to the fresh food product instead of the correct label. Accordingly, the technique disclosed by Japanese Unexamined Patent Application Publication No. 2008-165504 has difficulty in ensuring the safety of the fresh food product.

In Japanese Unexamined Patent Application Publication (Translation of PCT Application) No. 2006-504491, a scent is imparted to a pharmaceutical product. It is possible to have a pharmaceutical product impregnated with a scented substance in the production process; however, it is difficult to impart a scent to fresh food products, such as strawberries, in the process of growing the fresh food products.

Even if the technique of Japanese Unexamined Patent Application Publication No. 2008-165504 and that of Japanese Unexamined Patent Application Publication (Translation of PCT Application) No. 2006-504491 are combined, it is difficult to devise a technique for ensuring the safety of fresh food products with a simple method.

An information providing method according to an aspect of the present disclosure is an information providing method for an information providing system including a scent imparting apparatus, a scent detecting apparatus, and an information management apparatus, the information providing method including: adding, by the scent imparting apparatus, a scented substance to a plant; transmitting, by the scent imparting apparatus to the information management apparatus, product information that includes added-substance information indicating a first substance that is the scented substance and production information regarding the plant; receiving, by the information management apparatus, the product information; storing, by the information management apparatus, the product information in a production information storage unit; detecting, by the scent detecting apparatus, a second substance that is at least one of the scented substance or a metabolite of the scented substance released from a target plant; transmitting, by the scent detecting apparatus to the information management apparatus, detected-substance information indicating the second substance; receiving, by the information management apparatus, the detected-substance information; transmitting, by the information management apparatus to the scent detecting apparatus, in a case where the second substance indicated by the received detected-substance information is the same as the first substance indicated by the added-substance information included in the product information stored in the production information storage unit or is the same as a metabolite of the first substance, the production information included in the product information stored in the production information storage unit; receiving, by the scent detecting apparatus, the production information from the information management apparatus; and presenting, by the scent detecting apparatus, the received production information.

With this configuration, product information that includes added-substance information indicating a scented substance added to a plant and production information regarding the plant are stored, at least one of the scented substance or a metabolite of the scented substance released from the plant to which the scented substance is added is detected, and the production information of the plant that is a detection target is identified on the basis of the stored product information and detected-substance information indicating at least one of the detected scented substance or the detected metabolite.

Accordingly, a scented substance is added to a plant, and the scented substance added to the plant and production information of the plant are associated with each other. Therefore, when the added scented substance is compared with at least one of the detected scented substance or the detected metabolite, the production information of the plant can be easily identified, and the production information regarding the plant can be easily presented.

Further, in the information providing method described above, the scent imparting apparatus may further accepts input of the production information regarding the plant.

With this configuration, input of production information regarding a plant to which a scented substance is added is accepted, and therefore, for example, the production information input by the grower of the plant can be presented.

Further, in the information providing method described above, the plant may be a vegetable or fruit, or a fresh flower.

With this configuration, production information of a vegetable or fruit or production information of a fresh flower can be easily presented.

Further, in the information providing method described above, the scented substance may be a scented substance that is not contained in the plant.

With this configuration, a scented substance that is not contained in a plant is added, and therefore, production information associated with the scented substance added to the plant can be identified with certainty.

An information providing system according to another aspect of the present disclosure is an information providing system including: a scent imparting apparatus that adds a scented substance to a plant; a scent detecting apparatus that detects at least one of the scented substance or a metabolite of the scented substance released from the plant; and an information management apparatus, in which the scent imparting apparatus includes an adder that adds the scented substance to the plant, and a transmitter that transmits to the information management apparatus, added-substance information indicating the scented substance added to the plant and production information regarding the plant, the scent detecting apparatus includes a detector that detects at least one of the scented substance or the metabolite of the scented substance released from the plant, a transmitter that transmits to the information management apparatus, detected-substance information indicating at least one of the scented substance or the metabolite detected by the detector, a receiver that receives the production information from the information management apparatus, and a presenter that presents the production information received by the receiver, and the information management apparatus includes a first receiver that receives the added-substance information and the production information transmitted by the transmitter of the scent imparting apparatus, a production information storage unit that stores the added-substance information and the production information received by the first receiver in association with each other, a second receiver that receives the detected-substance information transmitted by the transmitter of the scent detecting apparatus, an identifier that identifies the production information of the plant that is a detection target on the basis of the added-substance information and the production information stored in the production information storage unit and the detected-substance information received by the second receiver, and a transmitter that transmits the production information identified by the identifier to the scent detecting apparatus.

With this configuration, added-substance information indicating a scented substance added to a plant and production information regarding the plant are stored in association with each other, at least one of the scented substance or a metabolite of the scented substance released from the plant to which the scented substance is added is detected, and the production information of the plant that is a detection target is identified on the basis of the stored added-substance information and the stored production information and on the basis of detected-substance information indicating at least one of the detected scented substance or the detected metabolite.

Accordingly, a scented substance is directly added to a plant, and the scented substance added to the plant and production information of the plant are associated with each other. Therefore, when the added scented substance is compared with at least one of a detected scented substance or a detected metabolite, the production information of the plant can be easily identified, and the production information regarding the plant can be easily presented.

A scent imparting apparatus according to another aspect of the present disclosure is a scent imparting apparatus for adding a scented substance to a plant, the scent imparting apparatus including: an adder that adds the scented substance to the plant; and a transmitter that transmits added-substance information indicating the scented substance added to the plant and production information regarding the plant to an information management apparatus that identifies the production information of the plant that is a detection target on the basis of the added-substance information and the production information and on the basis of detected-substance information indicating at least one of the scented substance or a metabolite of the scented substance released from the plant and detected by a scent detecting apparatus.

With this configuration, a scented substance is added to a plant, and production information of the plant that is a detection target is identified on the basis of added-substance information indicating the scented substance added to the plant and the production information regarding the plant and on the basis of detected-substance information indicating at least one of the scented substance or a metabolite detected from the plant.

Accordingly, a scented substance is added to a plant, the scented substance added to the plant and production information of the plant are associated with each other. When the added scented substance is compared with at least one of a detected scented substance or a detected metabolite, the production information of the plant can be easily identified, and the production information regarding the plant can be easily presented.

A scent detecting apparatus according to another aspect of the present disclosure is a scent detecting apparatus for detecting at least one of a scented substance or a metabolite of the scented substance released from a plant, the scent detecting apparatus including: a detector that detects at least one of the scented substance or the metabolite of the scented substance released from the plant; a transmitter that transmits detected-substance information indicating at least one of the scented substance or the metabolite detected by the detector; a receiver that receives from an information management apparatus that identifies, on the basis of added-substance information indicating the scented substance added to the plant, production information regarding the plant associated with the added-substance information, and the detected-substance information, the production information of the plant, the production information; and a presenter that presents the production information received by the receiver.

With this configuration, at least one of a scented substance or a metabolite of the scented substance released from a plant to which the scented substance is added is detected, and production information of the plant that is a detection target is identified on the basis of added-substance information indicating the scented substance added to the plant and the production information regarding the plant and on the basis of detected-substance information indicating at least one of the scented substance or the metabolite detected from the plant.

Accordingly, a scented substance added to a plant and production information of the plant are associated with each other, and at least one of the scented substance or a metabolite of the scented substance released from the plant to which the scented substance is added is detected. When the added scented substance is compared with at least one of the detected scented substance or the detected metabolite, the production information of the plant can be easily identified, and the production information regarding the plant can be easily presented.

An information management apparatus according to another aspect of the present disclosure includes: a first receiver that receives added-substance information transmitted by a scent imparting apparatus that adds a scented substance to a plant and indicating the scented substance added to the plant, and production information regarding the plant; a production information storage unit that stores the added-substance information and the production information received by the first receiver in association with each other; a second receiver that receives detected-substance information transmitted by a scent detecting apparatus that detects at least one of the scented substance or a metabolite of the scented substance released from the plant and indicating at least one of the detected scented substance or the detected metabolite; an identifier that identifies the production information of the plant that is a detection target on the basis of the added-substance information and the production information stored in the production information storage unit and the detected-substance information received by the second receiver; and a transmitter that transmits the production information identified by the identifier to the scent detecting apparatus.

With this configuration, added-substance information indicating a scented substance added to a plant and production information regarding the plant are stored in association with each other, and the production information of the plant that is a detection target is identified on the basis of the stored added-substance information and the stored production information and on the basis of detected-substance information indicating at least one of a detected scented substance or a detected metabolite.

Accordingly, a scented substance is added to a plant, and the scented substance added to the plant and production information of the plant are associated with each other. Therefore, when the added scented substance is compared with at least one of a detected scented substance or a detected metabolite, the production information of the plant can be easily identified, and the production information regarding the plant can be easily presented.

Hereinafter, an embodiment of the present disclosure will be described with reference to the attached drawings. Note that the following embodiment is an example embodiment of the present disclosure and is not intended to limit the technical scope of the present disclosure.

Embodiment

FIG. 1 is a diagram illustrating an overall configuration of an information providing system in the present embodiment.

The information providing system illustrated in FIG. 1 includes a scent imparting apparatus 1, a server apparatus 2, and scent detecting apparatuses 3 and 4. The server apparatus 2 is connected to each of the scent imparting apparatus 1 and the scent detecting apparatuses 3 and 4 via a network 5 so as to enable communication. The network 5 is, for example, the Internet.

The scent imparting apparatus 1 is used by a grower of vegetables or fruits or by an agent institution of the grower and adds a scented substance to the vegetables or fruits. Vegetables or fruits are examples of plants and are distributed to consumers from the grower. Targets to which the scent imparting apparatus 1 adds a scented substance may be fresh flowers. Targets to which the scent imparting apparatus 1 adds a scented substance are not limited to plants and may be, for example, fresh food products. The scented substance is, for example, a food additive, the use of which is permitted on the basis of the Food Sanitation Law.

The scent detecting apparatus 3 is used by a distributor that transports vegetables or fruits from growers to retailers and detects at least one of a scented substance or a metabolite of the scented substance released from a vegetable or fruit. Vegetables and fruits breathe. Therefore, a vegetable or fruit may release a scented substance taken therein as is, or may transform a scented substance taken therein to another compound by a chemical reaction caused by an enzyme or the like and release the compound obtained as a result of transformation as a metabolite. Note that in a case where plural distributors are involved in a distribution process of vegetables or fruits, the information providing system may include plural scent detecting apparatuses 3 for the respective distributors.

The scent detecting apparatus 4 is used by a retailer that sells vegetables or fruits or by a consumer who purchases vegetables or fruits and detects at least one of a scented substance or a metabolite of the scented substance released from a vegetable or fruit. Note that the scent detecting apparatus 3 and the scent detecting apparatus 4 have the same configuration.

Figure 2:
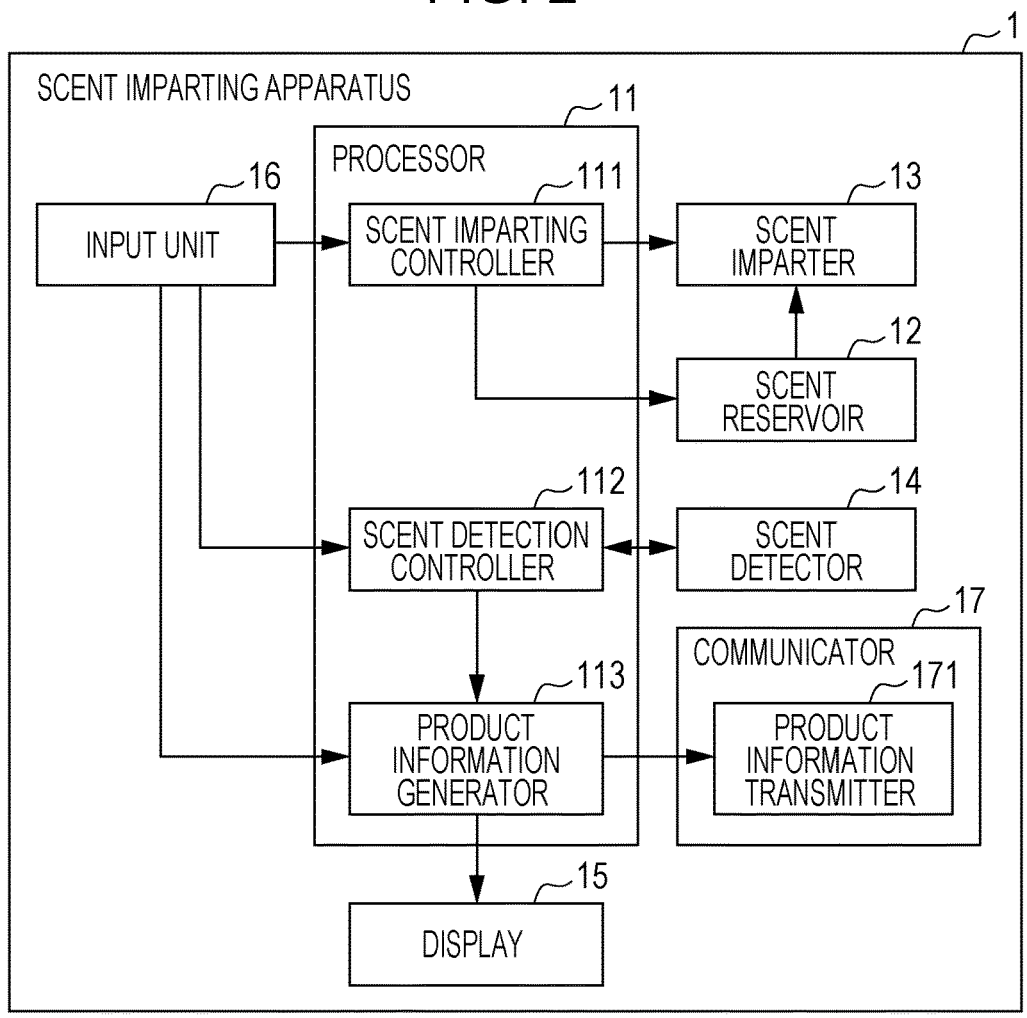
FIG. 2 is a block diagram illustrating a configuration of a scent imparting apparatus in the present embodiment.

FIG. 2 is a block diagram illustrating a configuration of the scent imparting apparatus in the present embodiment.

The scent imparting apparatus 1 illustrated in FIG. 2 includes a processor 11, a scent reservoir 12, a scent imparter 13, a scent detector 14, a display 15, an input unit 16, and a communicator 17.

The processor 11 includes a scent imparting controller 111, a scent detection controller 112, and a product information generator 113.

The input unit 16 is, for example, a touch panel, a keyboard, a mouse, or a switch and accepts an input operation by a grower.

The scent imparting controller 111 controls operations of the scent reservoir 12 and the scent imparter 13 on the basis of an input operation via the input unit 16. For example, a grower puts a vegetable or fruit in an enclosed space and inputs to the input unit 16 an addition start instruction for starting addition of a scented substance to the vegetable or fruit. The grower may input the type of a scented substance to be added to the vegetable or fruit via the input unit 16. In response to input of the addition start instruction via the input unit 16, the scent imparting controller 111 controls operations of the scent reservoir 12 and the scent imparter 13 so as to add the scented substance to the vegetable or fruit as instructed.

The scent reservoir 12 stores different types of scented substances. The scent reservoir 12 supplies a scented substance specified by the scent imparting controller 111 to the scent imparter 13. The scent imparting controller 111 may notify the product information generator 113 of the type of scented substance for which an instruction is input.

The scent imparter 13 adds a scented substance to a vegetable or fruit. The scent imparter 13 fills an enclosed space in which a vegetable or fruit is put with a predetermined amount of scented substance supplied from the scent reservoir 12. When the vegetable or fruit is left within the enclosed space filled with the scented substance for a predetermined time, the vegetable or fruit absorbs the scented substance, and the scented substance is added to the vegetable or fruit. The scent imparting controller 111 may notify the product information generator 113 of the date and time the predetermined time later as the date and time when the scent imparter 13 added the scented substance to the vegetable or fruit, that is, the scent imparting date and time. Note that the scent imparter 13 may add a scented substance that is not contained in the vegetable or fruit. The scent imparter 13 may add a different scented substance depending on the vegetable or fruit. The scent imparter 13 may add plural different scented substances to the vegetable or fruit.

For example, in a case where a scented substance is added to a processed product, such as a pharmaceutical product, the surface of the processed product needs to be coated with the scented substance, and it is not easy to add the scented substance. On the other hand, in the present embodiment, plants, such as vegetables and fruits, breathe, and therefore, when a vegetable or fruit is put in an enclosed space filled with a scented substance, the scented substance can be easily added to the vegetable or fruit. Further, it is difficult to alter the scented substance directly added to the vegetable or fruit, and therefore, the safety of the vegetable or fruit can be ensured.

The type of scented substance is information for identifying what the scented substance is and, for example, may be the name of the scented substance.

The type of metabolite is information for identifying what the metabolite is and, for example, may be the name of the metabolite.

The scent detection controller 112 controls operations of the scent detector 14 on the basis of an input operation via the input unit 16. For example, a grower puts a vegetable or fruit in an enclosed space and inputs to the input unit 16 a detection start instruction for starting detection of the type of a scented substance released from the vegetable or fruit.

The scent detector 14 is, for example, a gas chromatograph mass spectrometer and detects the type of a scented substance added to a vegetable or fruit. When the type of a scented substance added to a vegetable or fruit is detected immediately after addition of the scented substance, the type of the scented substance added to the vegetable or fruit can be detected. The scent detector 14 outputs the detected type of scented substance to the scent detection controller 112. The scent detection controller 112 outputs to the product information generator 113 the type of scented substance detected by the scent detector 14 as added-substance information indicating the scented substance added to the vegetable or fruit.

The product information generator 113 generates product information that includes added-substance information indicating a scented substance added to a vegetable or fruit and production information regarding the vegetable or fruit. The product information generator 113 displays on the display 15 a product information input screen for accepting input, by a grower, of production information and added-substance information regarding a vegetable or fruit. FIG. 7 illustrates an example of the product information input screen. The grower inputs production information via the input unit 16. The production information includes, for example, the product lot, the harvesting date, the product name (that is, the type of vegetable or fruit), grower information indicating the name of the grower, the shipping date and time, the destination of shipment, and the transport operator. When the product information input screen is displayed, the grower inputs added-substance information via the input unit 16. The added-substance information includes the type of a scented substance added to the vegetable or fruit, the type of a metabolite generated from the added scented substance by metabolism of the vegetable or fruit, the date and time when the scented substance was added, the scent detection result indicating whether the added scented substance was detected, and the scent detecting person.

The grower need not input the type of scented substance and the date and time when the scented substance was added, and the product information generator 113 may write to the product information input screen, the type of scented substance and the scent imparting date and time communicated from the scent imparting controller 111.

The grower need not input the type of scented substance, and the product information generator 113 may write to the product information input screen, the type of scented substance communicated from the scent detection controller 112.

The grower need not input the type of metabolite, and the product information generator 113 may write the type of metabolite obtained with a method described below to the product information input screen.

The scent imparting apparatus 1 may include a memory that stores in advance a table in which a type of vegetable or fruit, a type of scented substance, and a type of metabolite generated by the vegetable or fruit when the scented substance is added to the vegetable or fruit are associated with one another. In this case, the product information generator 113 reads a type of metabolite associated with the type of vegetable or fruit and with the type of added scented substance from the memory to obtain the type of metabolite.

The display 15 is, for example, a liquid crystal display and displays the product information input screen for a vegetable or fruit to accept input of production information of a vegetable or fruit and added-substance information from the grower.

The communicator 17 includes a product information transmitter 171. The product information transmitter 171 transmits to the server apparatus 2 product information that includes added-substance information indicating a scented substance added to a vegetable or fruit and production information regarding the vegetable or fruit to which the scented substance is added. The scent imparting apparatus 1 may generate the above-described product information for each product lot and transmit the product information generated for each product lot to the server apparatus 2.

Note that in the present embodiment, the scent imparting apparatus 1 includes the scent detection controller 112 and the scent detector 14; however, the present disclosure is not limited to this. The product information generator 113 may obtain the type of a scented substance added by the scent imparter 13 from the scent imparting controller 111. In this case, the scent detection controller 112 or the scent detector 14 is not necessary.

Figure 3:
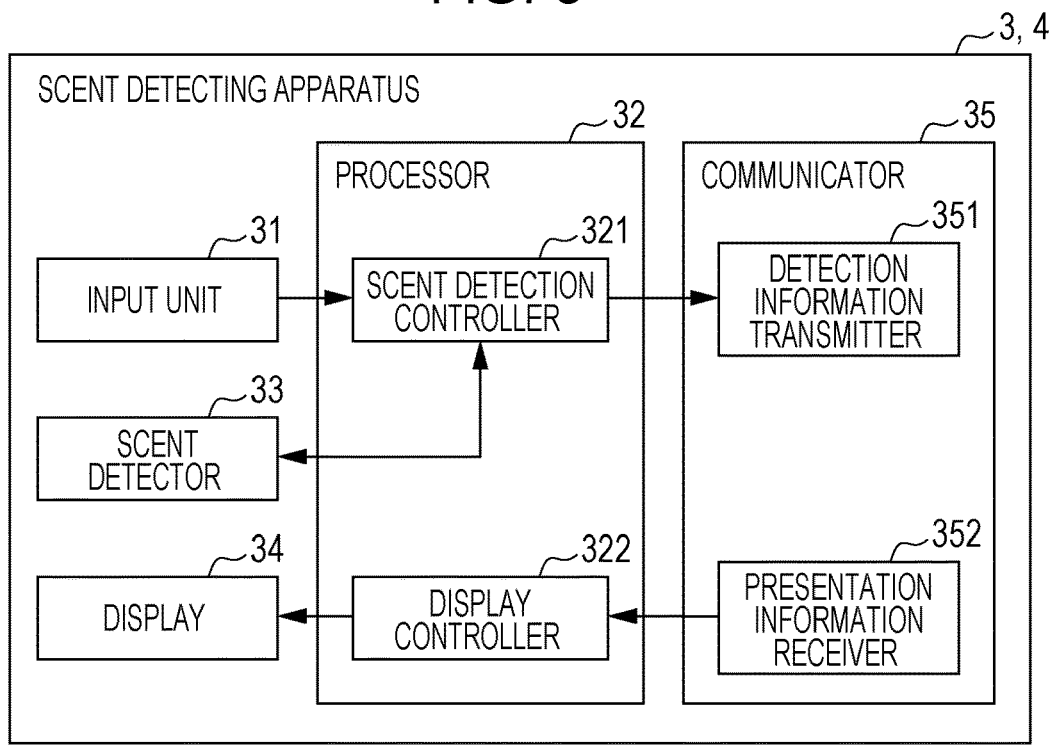
FIG. 3 is a block diagram illustrating a configuration of a scent detecting apparatus in the present embodiment.

FIG. 3 is a block diagram illustrating a configuration of the scent detecting apparatus in the present embodiment.

The scent detecting apparatus 3 illustrated in FIG. 3 includes an input unit 31, a processor 32, a scent detector 33, a display 34, and a communicator 35. Note that the configuration of the scent detecting apparatus 4 is the same as the configuration of the scent detecting apparatus 3.

The input unit 31 is, for example, a touch panel, a keyboard, a mouse, or a switch and accepts an input operation by a distributor or by a retailer.

The processor 32 includes a scent detection controller 321 and a display controller 322. The communicator 35 includes a detection information transmitter 351 and a presentation information receiver 352.

The scent detection controller 321 controls operations of the scent detector 33 on the basis of an input operation via the input unit 31. For example, a distributor or a retailer puts a vegetable or fruit in an enclosed space and inputs to the input unit 31 a detection start instruction for starting detection of the type of at least one of a scented substance or a metabolite of the scented substance released from the vegetable or fruit.

The scent detector 33 is, for example, a gas chromatograph mass spectrometer and detects the type of at least one of a scented substance or a metabolite of the scented substance released from a vegetable or fruit.

Plants, such as vegetables and fruits, breathe, release a scented substance added thereto, or transform the added scented substance to another compound and release the compound obtained as a result of transformation as a metabolite. Therefore, the scent detector 33 detects the type of a scented substance released from a vegetable or fruit, detects the type of a metabolite released from a vegetable or fruit, or detects the types of both a scented substance and a metabolite released from a vegetable or fruit. Note that it is not always the case that one type of metabolite is released from a vegetable or fruit to which one type of scented substance is added, and plural types of metabolites may be released.

The scent detector 33 outputs the detected type of at least one of the scented substance or the metabolite to the scent detection controller 321. The scent detection controller 321 outputs to the detection information transmitter 351 the type of at least one of the scented substance or the metabolite detected by the scent detector 33 as detected-substance information indicating at least one of the scented substance or the metabolite detected from the vegetable or fruit.

The detection information transmitter 351 transmits the detected-substance information indicating the type of at least one of the scented substance or the metabolite detected by the scent detector 33 to the server apparatus 2.

The presentation information receiver 352 receives presentation information including production information regarding a vegetable or fruit from the server apparatus 2.

The display controller 322 controls operations of the display 34 and outputs presentation information including production information received by the presentation information receiver 352 to the display 34 to display the presentation information on the display 34.

The display 34 presents presentation information including production information received by the presentation information receiver 352.

Figure 4:
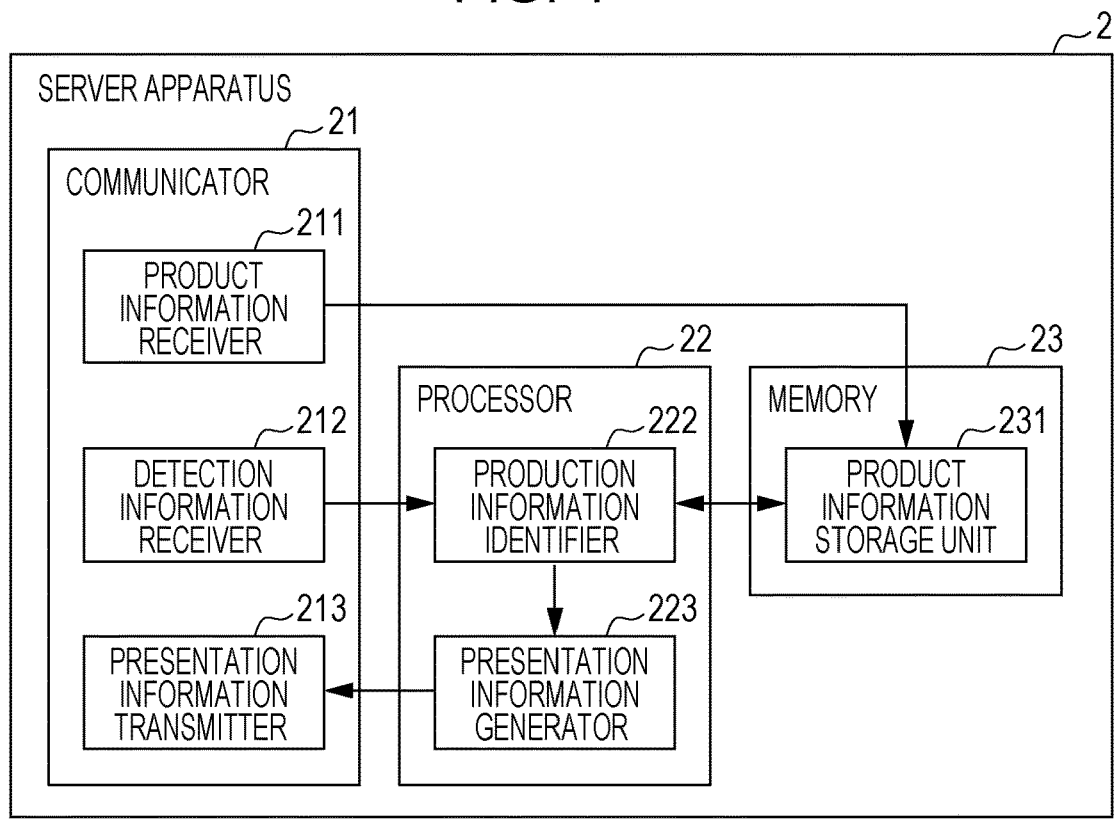
FIG. 4 is a block diagram illustrating a configuration of a server apparatus in the present embodiment.

FIG. 4 is a block diagram illustrating a configuration of the server apparatus in the present embodiment.

The server apparatus 2 is an example of the information management apparatus. The server apparatus 2 illustrated in FIG. 4 includes a communicator 21, a processor 22, and a memory 23.

The communicator 21 includes a product information receiver 211, a detection information receiver 212, and a presentation information transmitter 213. The processor 22 includes a production information identifier 222 and a presentation information generator 223. The memory 23 includes a product information storage unit 231.

The product information receiver 211 receives product information including added-substance information and production information transmitted by the scent imparting apparatus 1. The product information receiver 211 may receive product information for each product lot transmitted by the scent imparting apparatus 1. The product information receiver 211 stores the received added-substance information and production information in the product information storage unit 231 in association with each other. Note that in the present embodiment, the product information receiver 211 stores in the product information storage unit 231 the product information in which the added-substance information and the production information are associated with each other.

The product information storage unit 231 stores product information received by the product information receiver 211. The product information storage unit 231 stores product information, received by the product information receiver 211, in which added-substance information and production information are associated with each other.

The product information storage unit 231 may store product information for each product lot received by the product information receiver 211.

FIG. 5 is a diagram illustrating an example of product information stored in the product information storage unit in the present embodiment.

As illustrated in FIG. 5, each piece of product information includes, for example, the product lot, the harvesting date, the product name, grower information indicating the name of the grower, the type of a scented substance added to the vegetable or fruit, the type of metabolite, the date and time when the scented substance was added, the scent detection result indicating whether the added scented substance was detected, the scent detecting person, the shipping date and time, the destination of shipment, and the transport operator. In the product information, for example, the product lot, the harvesting date, the product name, grower information indicating the name of the grower, the shipping date and time, the destination of shipment, and the transport operator correspond to production information. In the product information, for example, the type of scented substance, the type of metabolite, the date and time when the scented substance was added, the scent detection result indicating whether the added scented substance was detected, and the scent detecting person correspond to added-substance information. The product information storage unit 231 stores product information for each product lot.

For example, product information of a vegetable or fruit includes the product lot "S00001", the harvesting date "4/1", the product name (the type of vegetable or fruit) "strawberry", grower information (the name of the grower) "AA", the type of scented substance "X", the type of metabolite "X1", the date and time when the scented substance was added "4/1, 10:00", the scent detection result indicating that the scented substance was detected, the person detecting the scented substance "CC", the shipping date and time "4/1, 15:00", the destination of shipment "EE", and the transport operator "GG".

Note that added-substance information may include only the type of scented substance and the type of metabolite. In a case where no metabolite is generated, added-substance information may include only the type of scented substance. Further, production information is not limited to that described above.

The detection information receiver 212 receives detected-substance information transmitted by the scent detecting apparatus 3. The detection information receiver 212 outputs the received detected-substance information to the production information identifier 222.

The production information identifier 222 identifies production information of a vegetable or fruit that is a detection target on the basis of added-substance information and production information stored in the product information storage unit 231 and detected-substance information received from the scent detecting apparatus 3. The production information identifier 222 reads from the product information storage unit 231 production information associated with added-substance information identified using the detected-substance information to thereby identify product information of the vegetable or fruit that is a detection target. The production information identifier 222 determines whether added-substance information that matches the type of at least one of a scented substance or a metabolite included in the detected-substance information received by the detection information receiver 212 is present in the product information storage unit 231. In a case where the production information identifier 222 determines that added-substance information that matches the type of at least one of a scented substance or a metabolite included in the detected-substance information is present in the product information storage unit 231, the production information identifier 222 reads production information associated with the added-substance information from the product information storage unit 231.

The production information identifier 222 may identify production information that corresponds to added-substance information stored in the product information storage unit 231 and including a type of scented substance or a type of metabolite that matches the type of substance (that is, scented substance or metabolite) detected from a vegetable or fruit and included in the detected-substance information received from the scent detecting apparatus 3. The added-substance information and the production information are included in the same product information. The production information identifier 222 may read the identified production information from the product information storage unit 231.

The production information identifier 222 may identify product information stored in the product information storage unit 231 and including added-substance information that includes a type of scented substance or a type of metabolite that matches the type of substance (that is, scented substance or metabolite) detected from a vegetable or fruit and included in the detected-substance information received from the scent detecting apparatus 3, and may read production information included in the identified product information from the product information storage unit 231.

A scented substance or a metabolite released from a vegetable or fruit decreases over time after addition of the scented substance. However, during a period until the vegetable or fruit is delivered to a retailer from the grower, a sufficient and detectable amount of scented substance remains in the vegetable or fruit. Therefore, the scented substance can be used as a tag of the vegetable or fruit.

The presentation information generator 223 generates presentation information including production information read by the production information identifier 222.

The presentation information transmitter 213 transmits presentation information including production information identified by the production information identifier 222 to the scent detecting apparatus 3.

Figure 6:
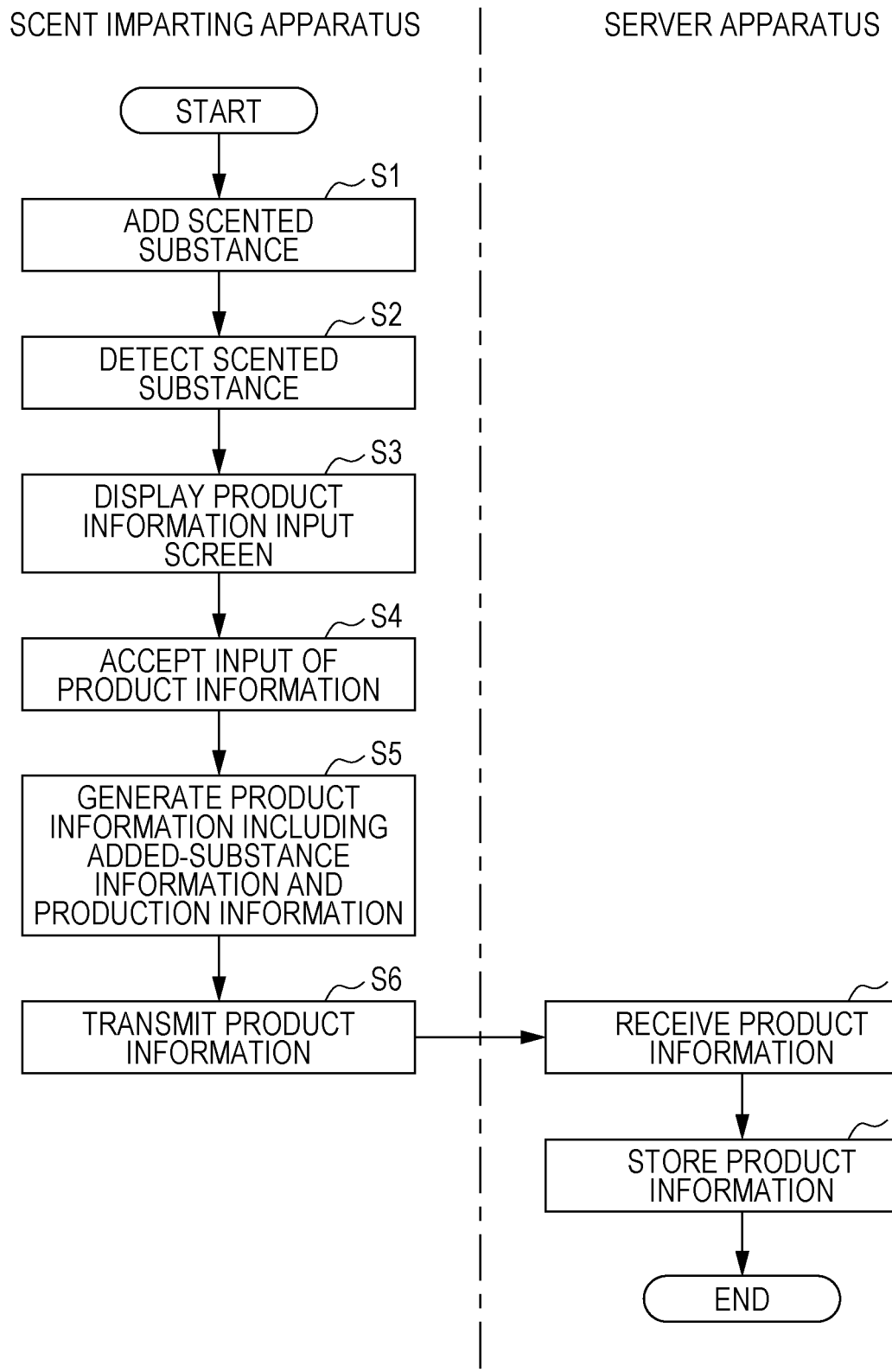
FIG. 6 is a flowchart for explaining a process in which the scent imparting apparatus transmits added-substance information and production information to the server apparatus in the present embodiment.

FIG. 6 is a flowchart for explaining a process in which the scent imparting apparatus transmits added-substance information and production information to the server apparatus in the present embodiment.

First, in step S1, the scent imparter 13 of the scent imparting apparatus 1 adds a scented substance to a vegetable or fruit in accordance with control from the scent imparting controller 111.

Next, in step S2, the scent detector 14 detects the scented substance added to the vegetable or fruit in accordance with control from the scent detection controller 112.

Next, in step S3, the product information generator 113 displays on the display 15 a product information input screen for accepting input, by the grower, of product information, that is, production information and added-substance information.

FIG. 7 is a diagram illustrating an example of the product information input screen in the present embodiment.

On a product information input screen 151 illustrated in FIG. 7, input fields for accepting input, by the grower, of product information, that is, production information and added-substance information, are displayed. On the product information input screen 151, input fields for accepting input, by the grower, of grower information, the harvesting date, the product name, the shipping date and time, the destination of shipment, the transport operator, the type of metabolite, the scent detecting person, and the product lot are displayed. Note that as the type of scented substance, the type of a scented substance added by the scent imparter 13 may be automatically displayed. As the scent imparting date and time, the date and time when the scented substance was added by the scent imparter 13 may be automatically displayed. The type of metabolite may be input by the grower. Alternatively, when the product name (type of vegetable or fruit) is input, a type of metabolite corresponding to the type of vegetable or fruit and to the type of the added scented substance may be automatically displayed.

Next, in step S4, the input unit 16 accepts input of production information and added-substance information by the grower. The grower inputs information to each input field of the product information input screen 151 displayed on the display 15. As illustrated in FIG. 7, a transmit button 152 and an exit button 153 are displayed on the product information input screen 151. When the transmit button 152 is pressed, product information including added-substance information and production information is generated and transmitted. When the exit button 153 is pressed, the process ends without generating product information.

Next, in step S5, the product information generator 113 generates product information that includes added-substance information indicating the scented substance added to the vegetable or fruit and production information regarding the vegetable or fruit.

Next, in step S6, the product information transmitter 171 transmits the product information to the server apparatus 2. The product information transmitter 171 may transmit product information generated for each product lot to the server apparatus 2.

Next, in step S7, the product information receiver 211 of the server apparatus 2 receives the product information transmitted by the scent imparting apparatus 1. The product information receiver 211 may receive product information for each product lot transmitted by the scent imparting apparatus 1.

Next, in step S8, the product information receiver 211 stores the received product information in the product information storage unit 231.

Figure 8:
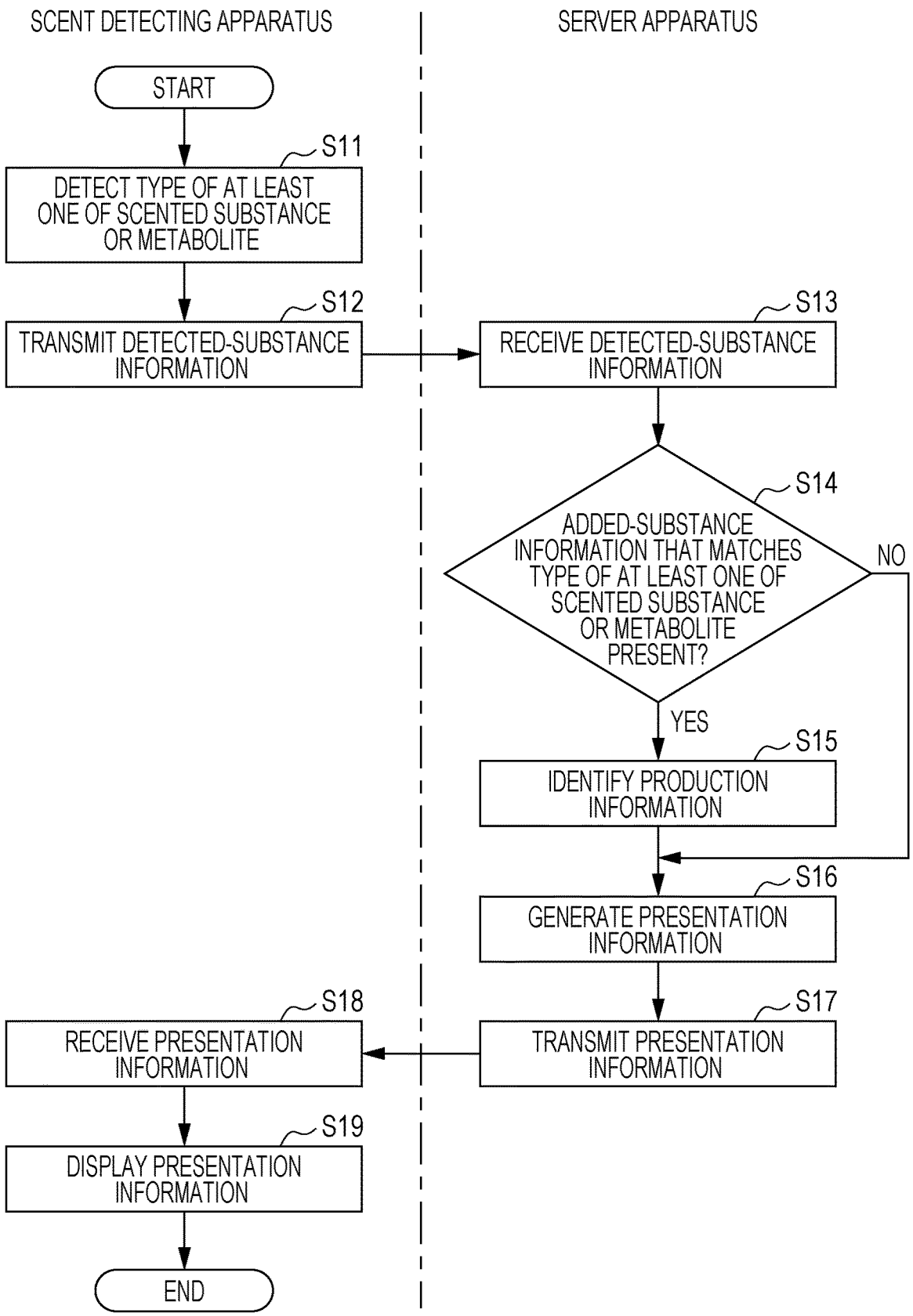
FIG. 8 is a flowchart for explaining a process in which production information is presented by the scent detecting apparatus and the server apparatus in the present embodiment.

FIG. 8 is a flowchart for explaining a process in which production information is presented by the scent detecting apparatus and the server apparatus in the present embodiment.

First, in step S11, the scent detector 33 of the scent detecting apparatus 3 detects the type of at least one of a scented substance or a metabolite released from a vegetable or fruit in accordance with control from the scent detection controller 321.

Next, in step S12, the detection information transmitter 351 transmits to the server apparatus 2 detected-substance information indicating the type of at least one of the scented substance or the metabolite detected by the scent detector 33.

Next, in step S13, the detection information receiver 212 of the server apparatus 2 receives the detected-substance information transmitted by the scent detecting apparatus 3.

Next, in step S14, the production information identifier 222 determines whether added-substance information that matches the type of at least one of the scented substance or the metabolite included in the detected-substance information received by the detection information receiver 212 is present in the product information storage unit 231.

In step S14, the production information identifier 222 may determine whether added-substance information including a type of scented substance or a type of metabolite that matches the type of substance (that is, scented substance or metabolite) detected from the vegetable or fruit and included in the detected-substance information received from the scent detecting apparatus 3 is stored in the product information storage unit 231.

In a case where the production information identifier 222 determines that added-substance information that matches the type of at least one of the scented substance or the metabolite included in the detected-substance information is present in the product information storage unit 231 (YES in step S14), in step S15, the production information identifier 222 reads production information associated with the added-substance information from the product information storage unit 231 to thereby identify production information of the vegetable or fruit that is a detection target.

In a case where added-substance information including a type of scented substance or a type of metabolite that matches the type of substance (that is, scented substance or metabolite) detected from the vegetable or fruit and included in the detected-substance information received from the scent detecting apparatus 3 is stored in the product information storage unit 231, in step S15, the production information identifier 222 may read production information included in identified product information from the product information storage unit 231 to thereby identify production information of the vegetable or fruit that is a detection target.

Next, in step S16, the presentation information generator 223 generates presentation information that includes the production information identified by the production information identifier 222.

On the other hand, in a case where the production information identifier 222 determines that added-substance information that matches the type of at least one of the scented substance or the metabolite included in the detected-substance information is not present in the product information storage unit 231 (NO in step S14), in step S16, the presentation information generator 223 generates presentation information for indicating that production information corresponding to the vegetable or fruit that is a detection target is not stored.

In a case where added-substance information including a type of scented substance or a type of metabolite that matches the type of substance (that is, scented substance or metabolite) detected from the vegetable or fruit and included in the detected-substance information received from the scent detecting apparatus 3 is not stored in the product information storage unit 231, in step S16, the presentation information generator 223 may generate presentation information for indicating that production information corresponding to the vegetable or fruit that is a detection target is not stored.

Next, in step S17, the presentation information transmitter 213 transmits the presentation information generated by the presentation information generator 223 to the scent detecting apparatus 3.

Next, in step S18, the presentation information receiver 352 of the scent detecting apparatus 3 receives the presentation information transmitted by the server apparatus 2.

Next, in step S19, the display controller 322 displays the presentation information received by the presentation information receiver 352 on the display 34. Here, in a case where the presentation information includes production information, the display 34 displays the presentation information including the production information. On the other hand, in a case where the presentation information indicates that production information corresponding to the vegetable or fruit that is a detection target is not stored, the display 34 displays the presentation information indicating that production information corresponding to the vegetable or fruit that is a detection target is not stored.

FIG. 9 is a diagram illustrating an example of presentation information including production information in the present embodiment. Presentation information 341 includes production information. The production information includes the product lot, grower information, the harvesting date, the product name, the shipping date and time, the destination of shipment, and the transport operator. For the presentation information 341, an exit button 343 is displayed. When the exit button 343 is pressed, the process ends.

As described above, added-substance information indicating a scented substance added to a vegetable or fruit and production information regarding the vegetable or fruit are stored in association with each other, at least one of the scented substance or a metabolite of the scented substance released from the vegetable or fruit to which the scented substance is added is detected, and production information of the vegetable or fruit that is a detection target is identified on the basis of the stored added-substance information and production information and detected-substance information indicating at least one of the detected scented substance or the detected metabolite. A scented substance is directly added to a vegetable or fruit, and the scented substance added to the vegetable or fruit and production information of the vegetable or fruit are associated with each other. Therefore, when the added scented substance is compared with at least one of the detected scented substance or the detected metabolite, the production information of the vegetable or fruit can be easily identified, and the production information of the vegetable or fruit can be easily presented.

Note that in the present embodiment, a scented substance is added to a vegetable or fruit and the scented substance released from the vegetable or fruit is detected, which enables not only identification of production information but also storage of a distribution log during a distribution process. That is, the display 34 of the scent detecting apparatus 3 may display a traceability information input screen for storing a distribution log by a distributor or by a retailer.

FIG. 10 is a diagram illustrating an example of the traceability information input screen in the present embodiment.

On a traceability information input screen 344 illustrated in FIG. 10, input fields for accepting input, by the distributor or the retailer, of the product lot, the product name, and the scent detecting person are displayed. Note that as the scent detection date and time, the date and time when at least one of a scented substance or a metabolite was detected by the scent detector 33 is automatically displayed. As the type of at least one of a scented substance or a metabolite, the type of at least one of the scented substance or the metabolite detected by the scent detector 33 is automatically displayed.

After the type of at least one of a scented substance or a metabolite has been detected by the scent detector 33 (after the process in step S11 in FIG. 8), the display 34 displays the traceability information input screen 344. The distributor or the retailer inputs information to each input field of the traceability information input screen 344 displayed on the display 34. As illustrated in FIG. 10, on the traceability information input screen 344, a transmit button 345 and an exit button 346 are displayed. When the transmit button 345 is pressed, traceability information is generated and transmitted. When the exit button 346 is pressed, the process ends without generating traceability information.

The traceability information includes, for example, the product lot, the product name, the scent detecting person, the scent detection date and time when at least one of a scented substance or a metabolite was detected, and the type of at least one of the scented substance or the metabolite.

The communicator 35 transmits the traceability information to the server apparatus 2. The communicator 21 of the server apparatus 2 receives the traceability information transmitted by the scent detecting apparatus 3. The communicator 21 stores the received traceability information in the memory 23. Thereafter, processes the same as the processes in step S14 and step S15 in FIG. 8 are performed, and the presentation information generator 223 generates presentation information that includes production information identified by the production information identifier 222 and detection result information indicating the result of detection of the scented substance in the distribution process.

Figures 11, 12:
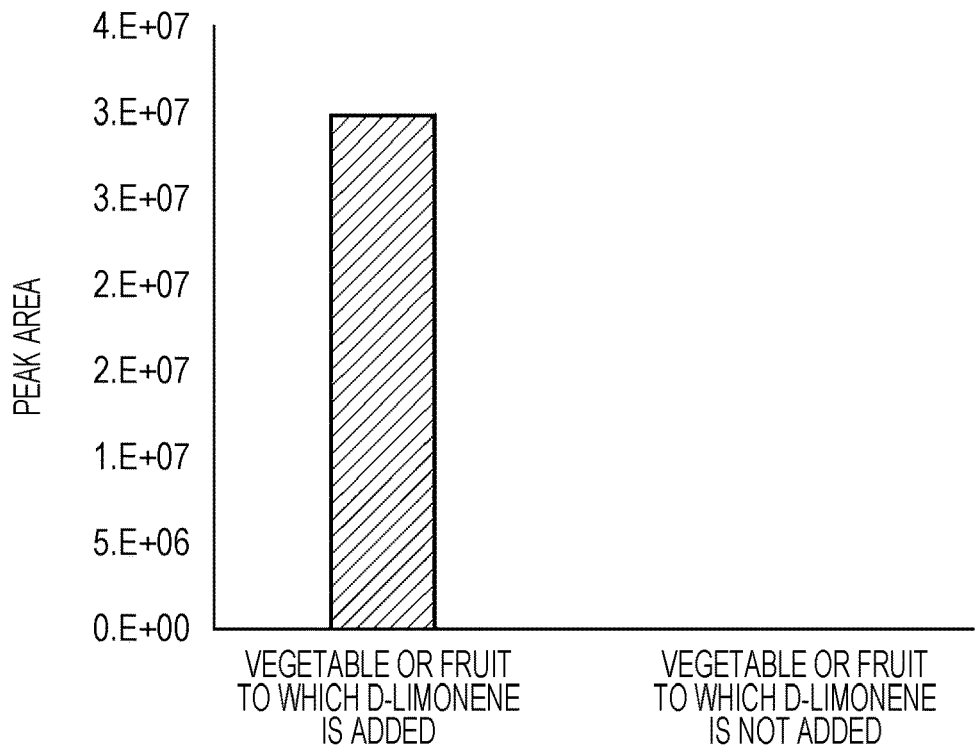
FIG. 11 is a diagram illustrating an example of presentation information including production information and detection result information in the present embodiment.
FIG. 12 is a diagram illustrating the detected amount of d-limonene released from a vegetable or fruit to which d-limonene is added and the detected amount of d-limonene released from a vegetable or fruit to which d-limonene is not added.

FIG. 11 is a diagram illustrating an example of presentation information including production information and detection result information in the present embodiment.

The display 34 displays presentation information 347 on a traceability result screen. The presentation information 347 includes production information and detection result information. The production information includes the product lot, grower information, the harvesting date, the product name, the shipping date and time, the destination of shipment, and the transport operator. The detection result information indicates the result of detection of a scented substance in the distribution process. First scent detection indicates whether the scented substance is detected when the scented substance is added to the vegetable or fruit. Second scent detection indicates whether the scented substance or a metabolite is detected when a distributor picks up the vegetable or fruit. Third scent detection indicates whether the scented substance or a metabolite is detected when a retailer receives the vegetable or fruit. For the presentation information 347, an exit button 349 is displayed. When the exit button 349 is pressed, the process ends.

When the retailer checks the detection result information displayed on the traceability result screen, the retailer can know whether a scented substance is detected in the distribution process.

Note that the detection result information may include the date and time when a scented substance is detected at the time when the scented substance is added to the vegetable or fruit, the date and time when the scented substance is detected at the time when a distributor picks up the vegetable or fruit, and the date and time when the scented substance is detected at the time when a retailer receives the vegetable or fruit.

Now, the result of an experiment is described in which a scented substance was added to a vegetable or fruit and at least one of the scented substance or a metabolite released from the vegetable or fruit was measured a predetermined time later.

In the experiment, a strawberry was used as the vegetable or fruit, and d-limonene was used as the scented substance. First, the present inventors put a strawberry and a piece of filter paper impregnated with d-limonene in a plastic cup and sealed the plastic cup to thereby add the scented substance to the strawberry. The present inventors put a strawberry and a piece of filter paper not impregnated with d-limonene in a plastic cup and sealed the plastic cup to prepare the strawberry that is a comparison target.

Subsequently, the present inventors put the strawberry to which the scented substance was added in a sample bag, sealed the sample bag, and left the sample bag for two hours at room temperature. Next, the present inventors inserted Tenax TA (60/80) into the sample bag as an absorbent to absorb gas of 200 ml in the sample bag. Subsequently, the present inventors collected the gas from Tenax TA (60/80) that absorbed the gas by thermal desorption and analyzed the gas component using a gas chromatograph mass spectrometer (GC-MS).

FIG. 12 is a diagram illustrating the detected amount of d-limonene released from the vegetable or fruit to which d-limonene was added and the detected amount of d-limonene released from the vegetable or fruit to which d-limonene was not added. The detected amount is represented by the peak area of the spectrum of the gas component.

As illustrated in FIG. 12, d-limonene was detected from the strawberry to which d-limonene was added, and d-limonene was not detected from the strawberry to which d-limonene was not added. The present inventors compared the peak areas of the spectrum of d-limonene obtained by using the gas chromatograph mass spectrometer.

Accordingly, it was verified that d-limonene, which is a scented substance, could be used as a tag of a vegetable or fruit. That is, when a scented substance added to a vegetable or fruit and production information of the vegetable or fruit are associated in advance with each other and the scented substance released from the vegetable or fruit that is a detection target is detected, production information of the vegetable or fruit that is a detection target can be easily obtained.

Further, the present inventors carried out another experiment by using a scented substance different from that described above. In the other experiment, a strawberry was used as the vegetable or fruit, and trans-2-hexenal was used as the scented substance. First, the present inventors put a strawberry and a piece of filter paper impregnated with trans-2-hexenal in a plastic cup and sealed the plastic cup to thereby add the scented substance to the strawberry. The present inventors put a strawberry and a piece of filter paper not impregnated with trans-2-hexenal in a plastic cup and sealed the plastic cup to prepare the strawberry that is a comparison target.

Subsequently, the present inventors used a gas chromatograph mass spectrometer (GC-MS) to analyze a gas component released from the strawberry to which the scented substance was added. Here, the present inventors put the strawberry to which the scented substance was added in a sample bag, sealed the sample bag, and left the sample bag for two hours at room temperature. Next, the present inventors inserted Tenax TA (60/80) into the sample bag as an absorbent to absorb gas of 200 ml in the sample bag. Subsequently, the present inventors collected the gas from Tenax TA (60/80) that absorbed the gas by thermal desorption and analyzed the gas component using a gas chromatograph mass spectrometer.

Figure 13:
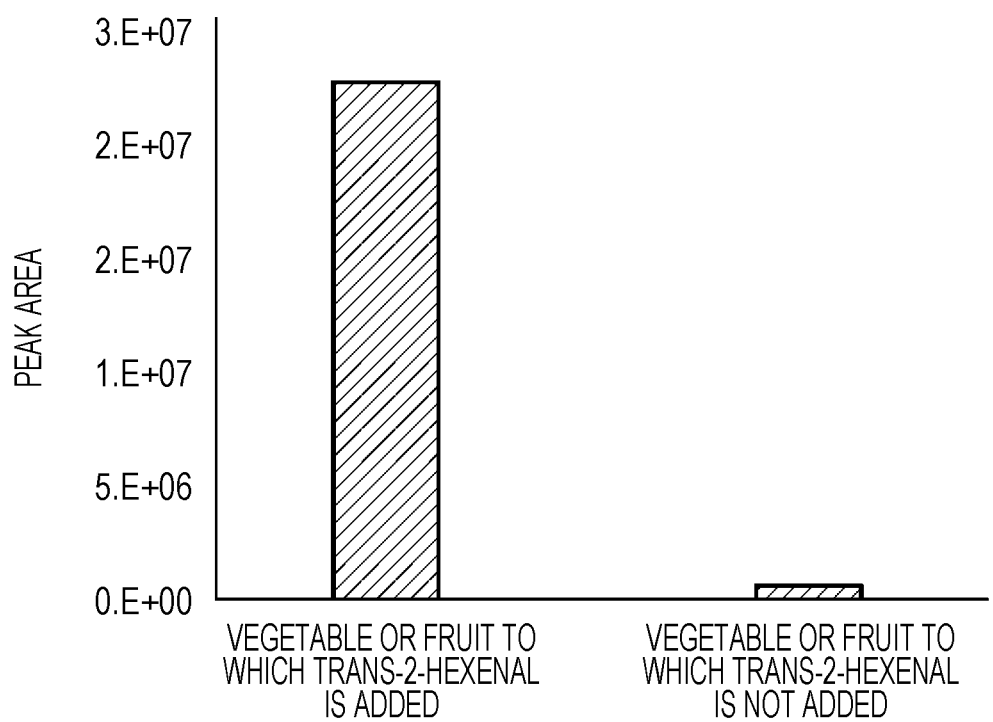
FIG. 13 is a diagram illustrating the detected amount of a metabolite released from a vegetable or fruit to which trans-2-hexenal is added and the detected amount of a metabolite released from a vegetable or fruit to which trans-2-hexenal is not added.

FIG. 13 is a diagram illustrating the detected amount of a metabolite released from the vegetable or fruit to which trans-2-hexenal was added and the detected amount of a metabolite released from the vegetable or fruit to which trans-2-hexenal was not added. The detected amount is represented by the peak area of the spectrum of the gas component.

As illustrated in FIG. 13, trans-2-hexenyl acetate, which is assumed to be a metabolite of trans-2-hexenal, was detected from the strawberry to which trans-2-hexenal was added, and almost no trans-2-hexenyl acetate was detected from the strawberry to which trans-2-hexenal was not added. The present inventors compared the peak areas of the spectrum of trans-2-hexenyl acetate obtained by using the gas chromatograph mass spectrometer.

Accordingly, it was verified that trans-2-hexenal, which is a scented substance, could be used as a tag of a vegetable or fruit. That is, when a metabolite of a scented substance added to a vegetable or fruit and production information of the vegetable or fruit are associated in advance with each other and the metabolite of the scented substance released from the vegetable or fruit that is a detection target is detected, production information of the vegetable or fruit that is a detection target can be easily obtained.

The present disclosure is not limited to the above-described embodiment. The embodiment to which various modifications conceived by a person skilled in the art are made and a form configured by combining constituent elements in different embodiments may be included in the scope of the present disclosure without departing from the spirit of the present disclosure.

Note that in the above-described embodiment, each constituent element may be configured as dedicated hardware or may be implemented by executing a software program suitable to the constituent element. Each constituent element may be implemented by a program executor, such as a CPU or a processor, reading a software program recorded to a recording medium, such as a hard disk or a semiconductor memory, and executing the software program.

Some or all of the functions of the apparatuses according to the embodiment of the present disclosure are typically implemented as an LSI (large-scale integration) integrated circuit. Each of the functions may be implemented as one chip, or one chip may include some or all of the functions. The circuit integration is not limited to LSI, and the functions may be implemented as a dedicated circuit or a general-purpose processor. An FPGA (field-programmable gate array) that can be programmable after LSI manufacture or a reconfigurable processor for which circuit cell connections and settings in LSI can be reconfigured may be used.

In the present disclosure, all or some of the units or devices, or all or some of the functional blocks of the block diagrams illustrated in FIG. 2 to FIG. 4 may be implemented as a semiconductor device, a semiconductor integrated circuit (IC), or one or more electronic circuits including LSI (large-scale integration).

Further, some or all of the functions of the apparatuses according to the embodiment of the present disclosure may be implemented by a processor, such as a CPU, executing a program.

Software for implementing the scent imparting apparatus in the present disclosure may cause a computer to perform steps included in the flowchart illustrated in FIG. 6.

Software for implementing the server apparatus in the present disclosure may cause a computer to perform steps included in the flowcharts illustrated in FIGS. 6 and 8.

Software for implementing the scent detecting apparatus in the present disclosure may cause a computer to perform steps included in the flowchart illustrated in FIG. 8.

Further, all numerals used in the above description are examples for specifically explaining the present disclosure, and the present disclosure is not limited to the example numerals.

The order in which steps in each flowchart described above are performed is an example for specifically explaining the present disclosure and the order may be other than that described above as long as similar advantages are attained. Further, some of the above-described steps may be performed simultaneously (in parallel) with the other steps.

Further, the present disclosure includes an information providing method described below.

An information providing method for an information providing system including a scent imparting apparatus that adds a scented substance to a plant, a scent detecting apparatus that detects at least one of the scented substance or a metabolite of the scented substance released from the plant, and an information management apparatus, the information providing method including:

adding, by the scent imparting apparatus, the scented substance to the plant;
transmitting, by the scent imparting apparatus to the information management apparatus, added-substance information indicating the scented substance added to the plant and production information regarding the plant;
receiving, by the information management apparatus, the added-substance information and the production information transmitted by the scent imparting apparatus;
storing, by the information management apparatus, the received added-substance information and the received production information in a production information storage unit in association with each other;
detecting, by the scent detecting apparatus, at least one of the scented substance or the metabolite of the scented substance released from the plant;
transmitting, by the scent detecting apparatus, detected-substance information indicating at least one of the detected scented substance or the detected metabolite to the information management apparatus;
receiving, by the information management apparatus, the detected-substance information transmitted by the scent detecting apparatus;
identifying, by the information management apparatus, the production information of the plant that is a detection target on the basis of the added-substance information and the production information stored in the production information storage unit and the detected-substance information received from the scent detecting apparatus;
transmitting, by the information management apparatus, the identified production information to the scent detecting apparatus;
receiving, by the scent detecting apparatus, the production information from the information management apparatus; and
presenting, by the scent detecting apparatus, the received production information.

The information providing method, the information providing system, the scent imparting apparatus, the scent detecting apparatus, and the information management apparatus according to the present disclosure enable easy presentation of production information regarding a plant, and therefore, are useful as an information providing method for providing information regarding a plant, an information providing system that provides information regarding a plant, a scent imparting apparatus that adds a scented substance to a plant, a scent detecting apparatus that detects at least one of a scented substance or a metabolite of the scented substance released from a plant, and an information management apparatus that manages information regarding a plant, respectively.

What is claimed is:

1. An information providing method for an information providing system including a scent imparting apparatus, a scent detecting apparatus, and an information management apparatus, the information providing method comprising:

adding, by the scent imparting apparatus, a scented substance to a plant;
transmitting, by the scent imparting apparatus to the information management apparatus, product information that includes added-substance information indicating a first substance that is the scented substance and production information regarding the plant;
receiving, by the information management apparatus, the product information;
storing, by the information management apparatus, the product information in a production information storage unit;
detecting, by the scent detecting apparatus, a second substance that is at least one of a scented substance or a metabolite of the scented substance released from a target plant that is the plant or another plant;

transmitting, by the scent detecting apparatus to the information management apparatus, detected-substance information indicating the second substance;

receiving, by the information management apparatus, the detected-substance information;

transmitting, when the second substance indicated by the received detected-substance information is the same as the first substance indicated by the added-substance information included in the product information stored in the production information storage unit or is the same as a metabolite of the first substance, by the information management apparatus to the scent detecting apparatus, the production information included in the product information stored in the production information storage unit;

receiving, by the scent detecting apparatus, the production information from the information management apparatus; and presenting, by the scent detecting apparatus, the received production information.

2. The information providing method according to claim 1, wherein
the scent imparting apparatus further accepts input of the production information regarding the plant.

3. The information providing method according to claim 1, wherein
the plant is a vegetable or fruit, or a fresh flower.

4. The information providing method according to claim 1, wherein
the scented substance is a scented substance that is not contained in the plant.

5. An information providing system comprising: a scent imparting apparatus that adds a scented substance to a plant; a scent detecting apparatus that detects at least one of the scented substance or a metabolite of the scented substance released from the plant; and an information management apparatus, wherein:
the scent imparting apparatus includes:
an adder that adds the scented substance to the plant, and
a transmitter that transmits to the information management apparatus, added-substance information indicating the scented substance added to the plant and production information regarding the plant;
the scent detecting apparatus includes:
a detector that detects at least one of the scented substance or the metabolite of the scented substance released from the plant,
a transmitter that transmits to the information management apparatus, detected-substance information indicating at least one of the scented substance or the metabolite detected by the detector,
a receiver that receives the production information from the information management apparatus, and
a presenter that presents the production information received by the receiver; and
the information management apparatus includes:
a first receiver that receives the added-substance information and the production information transmitted by the transmitter of the scent imparting apparatus,
a production information storage unit that stores the added-substance information and the production information received by the first receiver in association with each other,
a second receiver that receives the detected-substance information transmitted by the transmitter of the scent detecting apparatus, an identifier that identifies the production information of the plant that is a detection target on the basis of the added-substance information and the production information stored in the production information storage unit and the detected-substance information received by the second receiver, and
a transmitter that transmits the production information identified by the identifier to the scent detecting apparatus.

6. A scent imparting apparatus for adding a scented substance to a plant, the scent imparting apparatus comprising:
an adder that adds the scented substance to the plant; and
a transmitter that transmits added-substance information indicating the scented substance added to the plant and production information regarding the plant to an information management apparatus that identifies the production information of the plant that is a detection target on the basis of the added-substance information and the production information and on the basis of detected-substance information indicating at least one of the scented substance or a metabolite of the scented substance released from the plant and detected by a scent detecting apparatus.

7. A scent detecting apparatus for detecting at least one of a scented substance or a metabolite of the scented substance released from a plant, the scent detecting apparatus comprising:
a detector that detects at least one of the scented substance or the metabolite of the scented substance released from the plant;
a transmitter that transmits detected-substance information indicating at least one of the scented substance or the metabolite detected by the detector;
a receiver that receives from an information management apparatus that identifies, on the basis of added-substance information indicating the scented substance added to the plant, production information regarding the plant associated with the added-substance information, and the detected-substance information, the production information of the plant, the production information; and
a presenter that presents the production information received by the receiver.

8. An information management apparatus comprising:
a first receiver that receives added-substance information transmitted by a scent imparting apparatus that adds a scented substance to a plant and indicating the scented substance added to the plant, and production information regarding the plant;
a production information storage unit that stores the added-substance information and the production information received by the first receiver in association with each other;
a second receiver that receives detected-substance information transmitted by a scent detecting apparatus that detects at least one of the scented substance or a metabolite of the scented substance released from the plant and indicating at least one of the detected scented substance or the detected metabolite;
an identifier that identifies the production information of the plant that is a detection target on the basis of the added-substance information and the production information stored in the production information storage unit and the detected-substance information received by the second receiver; and a transmitter that transmits the production information identified by the identifier to the scent detecting apparatus.

\* \* \* \* \*